United States Patent [19]

Marti et al.

[11] Patent Number: 4,463,195
[45] Date of Patent: Jul. 31, 1984

[54] PROCESS FOR PRODUCING O-NITROBENZALDEHYDE

[75] Inventors: Hans-Rudolf Marti; René Gnehm, both of Küngoldingen, Switzerland

[73] Assignee: Siegfried Aktiengesellschaft, Zofingen, Switzerland

[21] Appl. No.: 484,842

[22] Filed: Apr. 14, 1983

[30] Foreign Application Priority Data

Apr. 19, 1982 [CH] Switzerland .......................... 2352/82

[51] Int. Cl.$^3$ ............................................. C07C 45/27
[52] U.S. Cl. ....................................... 568/424; 560/23
[58] Field of Search ................... 568/424, 435; 560/23

[56] References Cited

U.S. PATENT DOCUMENTS 3,287,393 11/1966 Akerstrom ..................... 560/23 X
4,203,928 5/1980 Meyer ................................ 568/424
4,297,519 10/1981 Ertel ................................... 568/424

FOREIGN PATENT DOCUMENTS 7503746 9/1975 Netherlands ..................... 568/424
21047 11/1904 United Kingdom ............. 568/435

Primary Examiner—Bernard Helfin
Attorney, Agent, or Firm—Werner W. Kleeman

[57] ABSTRACT

Ortho-nitrobenzaldehyde, a well known compound suitable as an indicator and as an intermediate for many organic syntheses including production of pharmaceuticals, is obtained by contacting a $C_1$–$C_4$ lower alkyl ester of o-nitrophenyl pyruvic acid in the form of its enolate, i.e. the enol salt or enol ester, with hydrogen peroxide; the enol salt can be the enolate of an alkali metal, an alkaline earth metal or of aluminum, and the enol ester can be the ester formed by the enolic hydroxyl and formic, acetic, propionic or butyric acid.

12 Claims, No Drawings

PROCESS FOR PRODUCING O-NITROBENZALDEHYDE

BACKGROUND OF THE INVENTION

This invention generally relates to the art of organic synthesis and specifically to the production of o-nitrobenzaldehyde.

Ortho-nitrobenzaldehyde, also referred to herein as ONBA for short, has the formula (1)

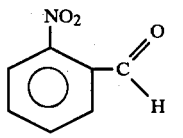

(1)

and one of the first methods for its production was disclosed as early as 1889 (German Pat. No. 48,722).

ONBA is a normally solid (commercially available ONBA melts at 42°–44° C.) pale-yellow substance that is almost insoluble in water but soluble in both polar and apolar organic solvents; it can be used, for example, as an indicator or reagent for isopropanol and acetone, as an intermediate product in the production of pharmaceutically active 4-(2-nitrophenyl)-1,4-dihydropyridines as disclosed, for example, in German published patent application (DE-OS) No. 16 70 827, and for other organic syntheses where a benzene ring with an aldehyde and nitro substituent is needed.

Yet, as recently as 1965–1968, ONBA has been said to be accessible with difficulties only (cf. Cassebaum, H., J. pr. Chem. Vol. 4, page 29 [1965] of Fieser, L. M. and M., Organische Chemie, Weinheim [1968], page 1004) and several new methods for producing ONBA have been suggested during the last decade.

A feature that is common to many ONBA syntheses including the most recent ones is to start from o-nitrotoluene which is contacted as such or in the form of a suitable derivative with an oxidizing agent; for example, use of chromic acid in acetic anhydride is suggested in Org. Syntheses, Coll. Vol. III, page 641, but large volumina are required and the product is obtained together with tarry by-products so as to require complicated recovery procedures.

Cassebaum (loc cit.) suggests to treat o-nitrotoluene with nitric acid for producing a nitrated intermediate (o-nitrophenyl nitromethane) which, in turn, is treated with potassium permanganate.

In an attempt to avoid the use of such oxidizing agents as potassium permanganate, one of the more recent synthesis methods disclosed, for example, in DE-OS No. 24 15 062 is based upon hydrolysis of o-nitrobenzylidene chloride

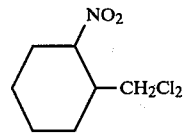

which, in turn, is obtained by treating o-nitrophenyl pyruvic acid with aqueous alkali metal hypochlorite; thus, the immediate precursor compound of ONBA is o-nitrobenzylidene chloride in this method.

The use of o-nitrophenyl pyruvic acid compounds as immediate precursors in the synthesis of ONBA has been suggested in DE-OS No. 24 15 061; the detour via the o-nitrobenzylidene chloride is avoided in that method and a salt of o-nitrophenyl pyruvic acid and an alkali metal as the precursor compound is contacted with potassium permanganate:

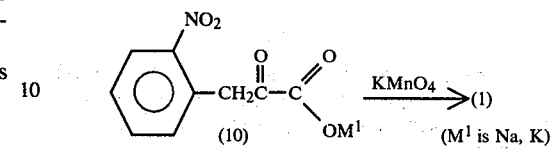

($M^1$ is Na, K)

While the precursor or salt of formula (10) can be conveniently obtained from o-nitrotoluene by reaction with a lower alkyl diester of oxalic acid in the presence of a lower alkanolate, such as sodium or potassium methylate, the use of potassium permanganate as the oxidizing agent is required again and causes most of the disadvantages that are typical for permanganate; this includes separation of the target compound ONBA from the manganic compounds that are obtained as a result of the reduction of the $MnO_4^-$ ion in the process, as well as waste water problems encountered with manganese compounds.

Thus, according to the art, no process of producing ONBA from the synthetically convenient o-nitrophenyl pyruvates is known where the target product may be obtained by treating the pyruvate precursor with an oxidizing agent that is more convenient than a permanganate.

SUMMARY OF THE INVENTION

Accordingly, a main object of this invention is to provide for a novel and improved method of producing o-nitrobenzaldehyde wherein the oxidizing agent used is hydrogen peroxide and wherein the target ONBA can be recovered directly and in satisfactory yields from the product of treating the o-nitrophenyl pyruvate precursor with the oxidizing agent.

Of course, hydrogen peroxide is well known for use as an oxidizing agent that produces but water and oxygen upon reductive decomposition and permits to avoid the problems typical for permanganate. Yet, it is most surprising and was clearly not obvious that hydrogen peroxide could be suitable as the oxidizing agent in ONBA synthesis; in fact, all previous studies (Mayer et al, Ann. 403 [1917] 167; Bachman et al, J. org. Chem. 8 [1943] 300; May et al, J. org. Chem. 11 [1946] 435) show that the use of hydrogen peroxide as an oxidizing agent for treating o-nitrophenyl pyruvic acid or salts thereof invariably leads to the formation of o-nitrophenyl acetic acid.

In contrast to the consistent teachings of the art, both with regard to the unsuitability of hydrogen peroxide and the actual prior teachings of other oxidizing agents, it has now been found according to the invention that ONBA can be obtained from an o-nitrophenyl pyruvate precursor by contacting or treating the latter with hydrogen peroxide if the α-carbonyl group of the pyruvate is maintained in enolic form and if the pyruvic carboxyl group is maintained in an esterified form when the precursor pyruvate is treated with the oxidizing agent.

Accordingly, the precursor used in the inventive process is an alkyl ester of o-nitrophenyl pyruvic acid in the form of the enol salt or enol ester having the formula (2)

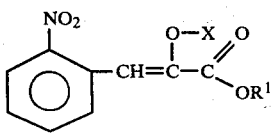

(2)

wherein $R^1$ in formula (2) is a $C_1$–$C_4$ alkyl, e.g. the methyl, ethyl, n-propyl, iso-propyl, n-butyl or iso-butyl radical; methyl, ethyl, iso-propyl and tert.-butyl are preferred as $R^1$ for many purposes, it being understood that selection of $R^1$ is mainly a matter of convenience and economy including preparation of the formula (2) compound because $R^1$ does not, of course, appear in the target product; methyl and ethyl are particularly preferred for $R^1$.

X in formula (2) is the atom or group attached to the enolic oxygen and the terms "enol salt", "enol ester" and "enolate" are used herein regardless of the nature of the bond between X and the enol oxygen. Suitable atoms for forming enolates include alkali metals, preferably sodium and potassium, earth alkaline metals including magnesium (preferred) and calcium, as well as aluminum, it being understood that if bivalent or trivalent atoms are involved only a monovalent residue of the atom would be attached to the enol oxygen, e.g. ½ Mg, ⅓ Al.

Suitable groups X for use in enol esters herein are monovalent residues of lower fatty acids, i.e. acyl groups of the formula

wherein $R^2$ is hydrogen or one of the $C_1$–$C_3$ alkyl groups enumerated above; methyl and ethyl are preferred for $R^2$ in many instances.

PREFERRED EMBODIMENTS OF THE INVENTION

Suitable compounds of the formula (2) are known per se and may, in general, be obtained by prior art methods. For example, the enol salts may be obtained in a manner known per se by reacting (I) o-nitrotoluene, (II) oxalic acid diester, e.g. the diethyl, dimethyl, dipropyl or dibutyl ester of oxalic acid, and (III) an alkanolate, such as the methylate, ethylate, propylate or butylate of sodium, potassium, magnesium or aluminum. The following scheme is given to illustrate production of formula (2) compounds:

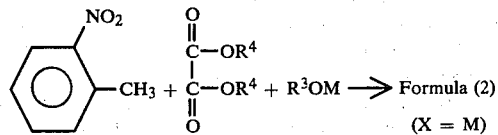

in which $R^2$ and $R^4$ are the same or different $C_1$–$C_4$ alkyls as illustrated above for $R^1$, M is selected from alkali metal atoms, e.g. Na or K, half of an earth alkaline metal atom, e.g. ½ Mg, or a third of an aluminum atom, i.e. ⅓ Al. Proper selection of $R^3$, $R^4$ and M is a matter of convenience, e.g. ease of reaction, availability and price. In general, the reaction just illustrated will be carried out in a liquid medium, such as an organic solvent, e.g. toluene, at autogenic temperatures. If the compound (2) for X=M is to be isolated, the reaction medium is preferably selected such that the compound can be crystallized from the solvent upon cooling; such isolation is not a necessary requirement and the reaction mixture obtained could be used directly for the inventive process.

Formula (2) compounds of the enol ester type (X=—C(O)$R^2$) may be obtained in a convenient manner by reacting an enol salt (formula 2, X=M) with a compound or compounds capable of attaching an acyl group of the formula defined above to the enol oxygen. Carboxylic acid anhydrides such as acetic anhydride or acyl halides, e.g. acyl chlorides, are examples of suitable reactants for converting X=M into X=—C(O)$R^2$ in formula (2); preferably, this conversion is carried out in an inert (vis-a-vis the acylating agent) organic solvent and, again, the formula (2) compound need not be isolated for use in the inventive process if the solvent used in the production of the formula (2) precursor is suitable for use in the treatment with hydrogen peroxide.

The process of producing ONBA according to the invention involves treatment of the formula (2) compound with hydrogen peroxide; a "treatment" in the sense of the present invention is any method of contacting the formula (2) compound with hydrogen peroxide so that the product or mixture obtained will contain a substantial portion or yield of ONBA.

In general, optimum yields will be obtained if the method of contacting the formula (2) compound with hydrogen peroxide avoids or minimizes hydrolysis of the $R^1$ moiety. Accordingly, the use of elevated temperatures (above about 50° C.) is to be avoided as well as operation at a pH of below 7. This may include external cooling as well as addition of a base, e.g. a mineral base such as aqueous sodium hydroxide. Selection of a suitable base for pH control is not believed to be critical and other inorganic or organic bases could be used. For reasons of costs and convenience, strong inorganic bases of the type mentioned will be generally satisfactory in view of effectiveness of pH control and in view of avoiding unnecessary increases of volumina.

It is believed that pH control is important for suitable yields of the target product. A generally suitable pH range that should be maintained during the treatment of the formula (2) compound with hydrogen peroxide is the pH range of from at least 7 to less than 14, preferably 7 to 12, e.g. 8 to 9.

While a lower temperature limit is not believed to be essential, the rate of reaction may become relatively slow at extremely low temperatures so that the general temperature range of treating the compound (2) with hydrogen peroxide will extend from −10° C. to +50° C. The temperature range of from 0° to 30° C. is preferred and room temperature is suitable for many purposes.

Preferably, treatment of the formula (2) compound with the hydrogen peroxide is effected in the presence of a major portion of a liquid medium, e.g. using at least the same weight portion of liquid medium as of the formula (2) compound. Use of liquid medium in larger weight amounts up to 10 times the weight of compound (2) is possible. Larger amounts are not generally preferred. Thus, a preferred amount of liquid medium used for treatment of the formula (2) compound with the hydrogen peroxide will be in the range of 1 to 10 parts, by weight (preferably 2 to 5 parts by weight), of liquid medium per part, by weight, of compound (2).

Preferably, the hydrogen peroxide for treating the formula (2) compound is used in an aqueous form, i.e. mixed with water. For example, hydrogen peroxide is available commercially in the form of aqueous solutions containing 20 to 70%, by weight, of hydrogen peroxide and such relatively concentrated aqueous forms may be used in the present process as a constituent of the liquid medium. The actual amount of hydrogen peroxide, calculated as pure $H_2O_2$, used for treating the formula (2) compound will, of course, be at least the stoichiometrically required amount and preferably more. Thus, at least one mol of $H_2O_2$ and generally 2 to 10 mol of $H_2O_2$, preferably 3 to 7 mol of $H_2O_2$, will be used per mol of compound (2).

As water is formed from the hydrogen peroxide during treatment of the formula (2) compound and because the hydrogen peroxide will generally be used in aqueous form, the liquid reaction medium will include an aqueous or hydrophilic portion which, in addition to the water formed or introduced by the hydrogen peroxide and, optionally, by adding an aqueous base, may include a water-miscible organic solvent such as a lower alkanol.

The liquid reaction medium may and frequently will include a non-aqueous or oleophilic portion such that the reaction medium is capable to form a two-phase system of two discrete or mutually "immiscible" liquid phases.

Notwithstanding the term "immiscible", an intimate contact between the formula (2) compound and the aqueous hydrogen peroxide should be achieved, generally by mechanically stirring the reaction mixture including the liquid medium. Accordingly, the mixture should be stirred with sufficient intensity for mutual interdispersion of any separate phases.

Examples of suitable water-immiscible organic solvents for use in a two-phase system include aromatic and saturated aliphatic hydrocarbons as well as halogenated hydrocarbons of both the aromatic and the aliphatic species and specific examples include toluene, dichloromethane and the like organic solvents. It will be understood that any water-miscible solvents present in the hydrophilic phase may and preferably should be soluble, to some extent at least, in the oleophilic phase. This may help to improve optimum contacting of the formula (2) compound when the latter is dissolved, at least in part, in the hydrophobic phase.

Treatment of the formula (2) compound with hydrogen peroxide will, in general, be effected under normal ambient pressure; reaction times may be between some minutes to several hours depending upon other reaction parameters including temperature, concentration and intensity of agitation. A reaction time of 10 to 60 minutes is typical for many instances.

As apparent from the above, the result of treating a formula (2) compound with hydrogen peroxide will always be a reaction mixture that includes an aqueous portion and—as the target ONBA is virtually insoluble in water—an organic portion. Thus, product recovery might simply be removal of liquid (aqueous, water-miscible organic solvents) components of the reaction mixture; frequently, product recovery will include working up a solution of ONBA in an organic solvent that may, but need not, be part of the liquid reaction medium and preferably is not miscible with water.

For example, the liquid reaction medium might include a water-miscible solvent, such as a lower alkanol, for ONBA as well as aqueous hydrogen peroxide but no water-imiscible organic solvent. Upon completion of the reaction, a water-immiscible organic solvent for ONBA may be added to take up most of the ONBA and water may be added to take up any water-soluble salts formed in the reaction as well as any water-soluble base added to the reaction.

Use of a suitable organic solvent as a constituent of the liquid reaction medium or as an addition for recovery of ONBA from the reaction mixture will facilitate recovery of the target product. It is believed to be an advantage of the inventive process that any by-products formed in the treatment of a compound of formula (2) with hydrogen peroxide will be either essentially water-soluble or volatile; further, the enolic salts and esters of formula (2) are sufficiently reactive with hydrogen peroxide so that presence of unreacted starting compound (2) in the reaction mixture obtained by treatment of (2) with hydrogen peroxide is avoided and does not complicate product recovery. Organic solvents suitable as a component of the oleophilic portion of the reaction medium and/or for product recovery by extraction of ONBA from the reaction mixture include aromatic hydrocarbons, such as benzene or toluene, aliphatic hydrocarbons, such as hexane or heptane, halogenated hydrocarbons, such as methylene dichloride or chloroform, and the like organic solvents including ethers, esters and ketones.

The following examples are given to illustrate but not limit the invention. Parts and percentages are by weight. Temperatures are in degree centigrade.

EXAMPLE 1

This example illustrates production of a formula (2) enol salt (K) of a lower alkyl (ethyl) ester of o-nitrophenyl pyruvic acid. The reaction is as follows:

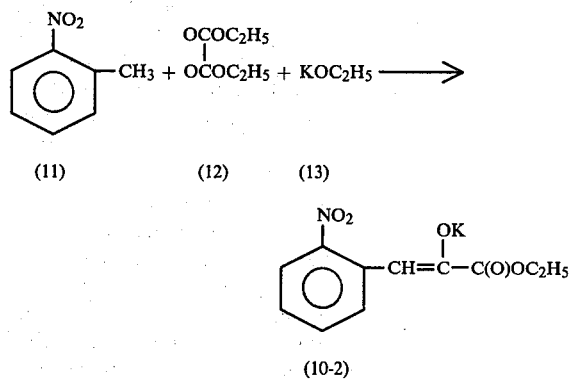

360 g (2.63 mol) of o-nitrotoluene and 500 g (3.42 mol) of the diethyl ester of oxalic acid are charged into a reaction flask (4.5 liters capacity) provided with 2000 ml of toluene. The flask content is agitated with a mechanical stirrer while a total of 236 g (2.81 mol) of potassium ethylate is added in two portions.

The heat of reaction caused an increase of the temperature of the reaction mixture of up to 80° C. while the target enol salt of formula (10-2) began to precipitate. The reaction mixture was allowed to cool to room temperature and a mass of precipitated crystalline enol salt (10-2) was recovered on a suction filter. The dark-red crystals were washed with toluene and dried in an oven with forced air circulation to yield 704 g (2.56 mol; 97.3% of the theoretical yield based upon the o-nitrotoluene) of the formula (10-2) enol salt.

Other compounds of formula (2; X=M) may be obtained in this manner if the alkyl moieties of compounds (12) and (13) are replaced by other $C_1$–$C_4$ alkyl groups or if the potassium in compound (13) is replaced by sodium, ½ Mg or ⅓ Al, while the ethyl moiety in compound (13) is replaced by methyl and iso-propyl. Preferred metal alcoholates include the methylate or ethylate of sodium or potassium, the ethylate of magnesium and the iso-propylate of aluminum.

EXAMPLE 2

This example illustrates the production of an enol ester (acetyl) of the ethyl ester of o-nitrophenyl pyruvic acid. The reaction is as follows:

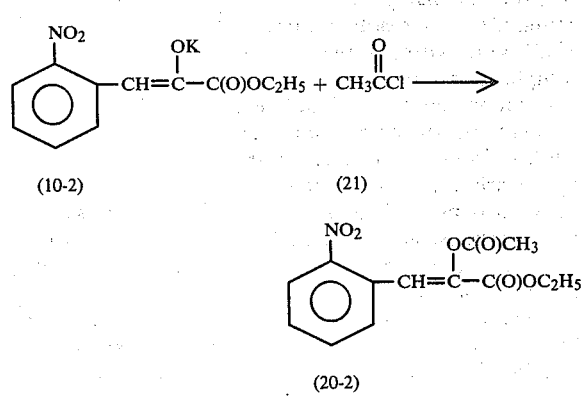

275.3 g (1 mol) of the enol salt of the formula (10-2) obtained according to the procedure of example 1 were introduced into a reaction flask (capacity of 1.5 liters) charged with 800 ml of dichloromethane and suspended in the liquid. The suspension was cooled by agitating the flask content while the flask was on an ice bath. 78.8 g (1 mol) of acetyl chloride were added slowly so that the reaction temperature was maintained at 5° to 10° C.

Subsequently, the reaction mixture was heated to 40° C. for a period of 60 minutes, allowed to cool and transferred into a funnel where 500 ml of water were added. After shaking and subsequent phase separation the organic phase was removed and concentrated in a rotary evaporator. Then, 300 ml of absolute ethanol were added to precipitate a crystalline product that was recovered on a suction filter and washed with ethanol on the filter. This product is the enol ester of formula (20-2) obtained in an amount of 178.7 g (0.64 mol; yield is 64% of the theory) having a melting point of 93.5° to 94.5° C.

Other compounds of formula (2) with

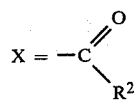

and $R^1 = C_1$–$C_4$ alkyl may be obtained in this manner if the alkyl moieties of the formula (10-2) and/or the formula (21) compound are replaced by other $C_1$–$C_4$ alkyls (in formula 10-2) and/or other $C_1$–$C_3$ alkyls (in formula 21).

EXAMPLE 3

This example illustrates the production of o-nitrobenzaldehyde (1) from a formula (2) compound

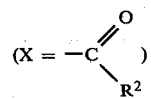

by treatment with aqueous hydrogen peroxide according to the inventive process. The reaction is as follows:

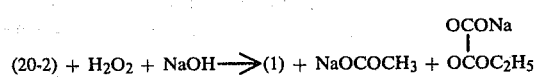

5.6 g (0.02 mol) of the compound of formula (20-2) prepared as disclosed in example 2 are mixed with 30 ml of ethanol. While this mixture is agitated vigorously with a mechanical stirrer, 5 g of a 50% aqueous solution of hydrogen peroxide and 6.5 g of a 30% aqueous solution of sodium hydroxide are added. The reaction causes an autogeneous temperature increase of up to 40° C. The mixture is allowed to cool to room temperature (20° to 25° C.) whereupon 50 ml of toluene are added. Then, water is added until the liquid phase shows formation of two separate layers and about 150 ml of water were required to achieve this.

The aqueous phase is separated and discarded; the organic phase is again washed with a small portion of water and then yields 1.9 g (0.013 mol=63% of the theoretical yield, based upon the formula 20-2 compound) of the formula (1) target compound, m.p. 41.5° to 42.5° C., upon concentration.

Similar results will be obtained if the compound of the formula (20-2) used in this example is replaced by other formula (2) compounds where either or both of $R^1$ or $R^2$ (in

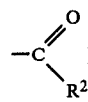

are varied as indicated in example 2.

EXAMPLE 4

This example illustrates the production of o-nitrobenzaldehyde (1) from a formula (2) compound (X=M) by treatment with aqueous hydrogen peroxide according to the invention. The reaction is as follows:

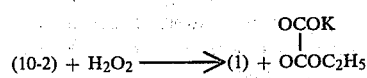

27.5 parts of the enol salt of formula (10-2) obtained as described in example 1 are added in incremental portions to a vigorously agitated mixture of 113 parts of toluene, 12 parts of a 30% aqueous sodium hydroxide solution and 20 parts of a 50% aqueous hydrogen peroxide solution. Agitation is effected by a mechanical stirrer and the reaction mixture is externally cooled on an ice bath. The rate of adding the enol salt (10-2) is controlled such that the temperature of the externally cooled reaction mixture is maintained at 10° to 15° C.

Addition is completed within a period of about 20 minutes. Subsequently, water is added until phase separation and the aqueous phase is discarded. The organic (toluene) phase is washed with a small portion of water and yields o-nitrobenzaldehyde, m.p. 41° to 43° C., upon concentration of the organic phase in a yield of about half the theoretical yield, based upon the enol salt.

Similar results will be obtained with the other formula (2) compounds that can be produced as described in example 1.

Various modifications of the above disclosed specific embodiments of the invention will be readily apparent to those skilled in the art. It is the applicants' intention to cover by their claims all those changes and modifications which could be made to the embodiments of the invention herein chosen for purposes of the disclosure without departing from the spirit and scope of the invention.

Protection by Letters Patent of this invention in all its aspects as the same are set forth in the appended claims is sought to the broadest extent that the prior art allows.

Accordingly, what is claimed is:

1. A process for producing o-nitrobenzaldehyde of the formula (1)

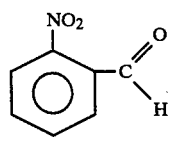
(1)

comprising the step of contacting an o-nitrophenyl pyruvate compound of the formula (2)

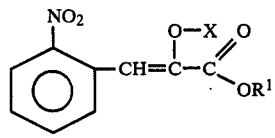
(2)

wherein $R^1$ is a $C_1$-$C_4$ alkyl group and X is a member selected from the group consisting of monovalent residues of alkali metal atoms, earth alkaline metal atoms and aluminum; and monovalent residues of the formula

in which $R^2$ is a member selected from the group consisting of hydrogen and $C_1$-$C_3$ alkyl groups; with hydrogen peroxide to form a mixture containing said o-nitrobenzaldehyde and recovering said o-nitrobenzaldehyde from said mixture.

2. The process of claim 1, wherein said formula (2) compound is an enol salt of the formula

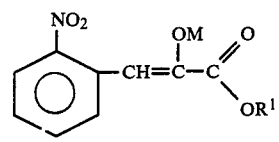

in which M is selected from the group consisting of Na, K, ½ Mg, ⅓ Al and $R^1$ is a $C_1$-$C_4$ alkyl group.

3. The process of claim 1, wherein said formula (2) compound is an enol ester of the formula

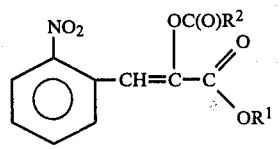

wherein $R^1$ is a $C_1$-$C_4$ alkyl group and $R^2$ is a member selected from the group consisting of hydrogen and $C_1$-$C_3$ alkyl groups.

4. A process of producing o-nitrobenzaldehyde comprising the steps of reacting o-nitrotoluene in the presence of an alcoholate of the formula $R^3OM$ wherein $R^3$ is a $C_1$-$C_4$ alkyl group, and M is a member selected from the group consisting of Na, K, ½ Ca, ½ Mg and ⅓ Al, with an oxalic diester of the formula

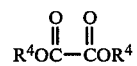

wherein each $R^4$ is a $C_1$-$C_4$ alkyl group, to produce an enol salt of the formula

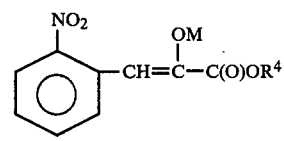

in which M and $R^4$ are as defined; reacting said enol salt with aqueous hydrogen peroxide at a pH of from 7 to 14 and a temperature of from $-10°$ C. to $+50°$ C. to form a reaction mixture containing said o-nitrobenzaldehyde; and recovering said o-nitrobenzaldehyde from said mixture.

5. A process of producing o-nitrobenzaldehyde comprising the steps of reacting o-nitrotoluene in the presence of an alcoholate of the formula $R^3OM$ wherein $R^3$ is a $C_1$-$C_4$ alkyl group, and M is a member selected from the group consisting of Na, K, ½ Ca, ½ Mg and ⅓ Al, with an oxalic diester of the formula

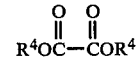

wherein each $R^4$ is a $C_1$-$C_4$ alkyl group, to produce an enol salt of the formula

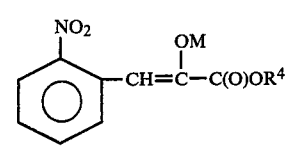

in which M and $R^4$ are as defined; acylating said enol salt to produce an enol ester of the formula

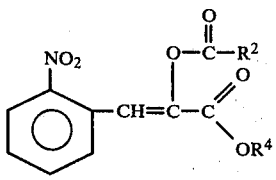

wherein $R^2$ is a $C_1-C_3$ alkyl group and $R^4$ is as defined above; reacting said enol ester with aqueous hydrogen peroxide at a pH of from 7 to 14 and a temperature of from $-10°$ C. to $+50°$ C. to form a reaction mixture containing said o-nitrobenzaldehyde; and recovering said o-nitrobenzaldehyde from said mixture.

6. The process of claim 4, wherein M is selected from sodium and potassium and wherein $R^3$ and $R^4$ are each selected from methyl and ethyl.

7. The process of claim 5, wherein M is selected from sodium and potassium and wherein $R^3$ and $R^4$ are each selected from methyl and ethyl.

8. The process of claim 5, wherein said enol salt is acylated by reaction with an acyl halide or a carboxylic acid anhydride.

9. The process of claim 8, wherein M is selected from sodium and potassium, $R^3$ and $R^4$ are each selected from methyl and ethyl.

10. The process of claim 8, wherein said enol salt is acylated by reaction with acetic anhydride or acetyl chloride.

11. The process of claim 1, wherein said treatment of said formula (2) compound with said hydrogen peroxide is effected in a liquid reaction medium that includes a hydrophilic portion.

12. The process of claim 11, wherein said liquid medium further includes an oleophilic portion that is substantially immiscible with said hydrophilic portion.

* * * * *